United States Patent
Wu et al.

(10) Patent No.: US 11,505,633 B2
(45) Date of Patent: Nov. 22, 2022

(54) THERMO-SENSITIVE CELL CULTURE SUBSTRATE HAVING BLOCK COPOLYMER

(71) Applicant: QINGDAO AMA CO., LTD, Jiaozhou (CN)

(72) Inventors: Pei-Yen Wu, Qingdao (CN); Zhenping Cheng, Qingdao (CN); Thai-Yen Ling, Taipei (TW); Meng-Shiue Wu, Taipei (TW)

(73) Assignee: QINGDAO AMA CO., LTD, Qingdao (CN)

( * ) Notice: Subject to any disclaimer, the term of this patent is extended or adjusted under 35 U.S.C. 154(b) by 263 days.

(21) Appl. No.: 16/840,654

(22) Filed: Apr. 6, 2020

(65) Prior Publication Data
US 2021/0155728 A1    May 27, 2021

(30) Foreign Application Priority Data

Nov. 25, 2019    (CN) .......................... 201911163920.4

(51) Int. Cl.
| | | |
|---|---|---|
| C08F 226/10 | (2006.01) | |
| C08F 220/18 | (2006.01) | |
| C08F 226/06 | (2006.01) | |
| C08F 293/00 | (2006.01) | |
| C12N 5/00 | (2006.01) | |
| C08K 5/3467 | (2006.01) | |

(Continued)

(52) U.S. Cl.
CPC ...... *C08F 220/1804* (2020.02); *C08F 226/06* (2013.01); *C08F 293/005* (2013.01); *C12N 5/0068* (2013.01); *C08F 216/18* (2013.01); *C08F 220/14* (2013.01); *C08F 220/16* (2013.01); *C08F 226/10* (2013.01); *C08F 2438/01* (2013.01); *C08F 2438/03* (2013.01); *C08K 5/3467* (2013.01)

(58) Field of Classification Search
None
See application file for complete search history.

(56) References Cited

U.S. PATENT DOCUMENTS

| | | |
|---|---|---|
| 8,278,097 B2 | 10/2012 | Kurosawa et al. |
| 9,279,102 B2 | 3/2016 | Nakayama et al. |
| 2019/0194376 A1* | 6/2019 | Maejima ............... C08F 293/00 |

FOREIGN PATENT DOCUMENTS

WO    WO-2016159153 A1 * 10/2016

OTHER PUBLICATIONS

Liu, X. et al., "Poly(vinylpyrrolidone-b-styrene) block copolymers tethered surfaces for protein adsorption and cell adhesion regulation". Colloids and Surfaces, B: Biointerfaces 2010, 79(2), 452-459. (Year: 2010).*

(Continued)

*Primary Examiner* — Richard A Huhn
(74) *Attorney, Agent, or Firm* — Locke Lord LLP; Tim Tingkang Xia, Esq.

(57) ABSTRACT

A method of preparing PNVCL block polymers as the substrate for thermo-sensitive cultureware is provided. A hydrophobic polymer of poly n-butyl mathacrylate (PBMA) is obtained by atom transfer radical polymerization (ATRP) with typical haloalkane as an initiator. Further a thermo-sensitive block copolymer of poly n-vinyl caprolactam (PNVCL) is obtained by polymerization of N-vinyl caprolactam (NVCL) monomers using the hydrophobic PBMA polymer as a macroinitiator.

6 Claims, 5 Drawing Sheets

LIGAND: 5,5,7,12,12,14-HEXAMETHYL-1,4,8,11-TETRA-AZACYCLOTETRADECANE (Me₆Cyclam)
BMA: BUTYL METHACRYLATE
NVCL: N-VINYLCAPROLACTAM (51) Int. Cl.
  *C08F 220/16* (2006.01)
  *C08F 220/14* (2006.01)
  *C08F 216/18* (2006.01)

(56) References Cited

OTHER PUBLICATIONS

Jiang et al., A novel poly(N-vinylcaprolactam)-based well-defined amphiphilic graft copolymer synthesized by successive RAFT and ATRP, Polym. Chem., 2013, 4, 1402.
Tsuda et al., Control of cell adhesion and detachment using temperature and thermoresponsive copolymer grafted culture surfaces, Graduate School of Science and Engineering, 2004.
Takahashi et al., Controlled chain length and graft density of thermoresponsive polymer brushes for optimizing cell sheet harvest, Biomacromolecules, 2010, 11, 1991-1999.
Wan et al., Controlled radical polymerization of N-vinylcaprolactam mediated by xanthate or dithiocarbamate, Journal of Polymer Science Part A Polymer Chemistry, 2008.
Thomassin et al., Double thermo-responsive hydrogels from poly(vinylcaprolactam) containing diblock and triblock copolymers, Polym. Chem., 2015, 6, 1856.
Li et al., Effect of block compositions of amphiphilic block copolymers on the physicochemical properties of polymeric micelles, Polymer, 2011, 52, 3783-3790.
Destarac et al., Macromolecular design via the interchange of xanthates (MADIX): polymerization of styrene with o-ethyl xanthates as controlling agents, Macromol. Chem. Phys., 2002, 203, 2281-2289.
Laschewsky, Novel amphiphilic diblock copolymers by RAFT-polymerization, their self-organization and surfactant properties, Dissertation.
Yu et al., One-pot synthesis of poly(N-vinylcaprolactam)-based biocompatible block copolymers using a dual initiator for ROP and RAFT polymerization, Polymer, 2013, 54, 6119-6124.
Liang et al., Poly(N-vinylcaprolactam) based thermoresponsive nanostructured materials, Dissertation.
Ozdemir et al., Polymerization of N-vinylcaprolactam and characterization of poly(N-vinylcaprolactam), Journal of Polymer Science Part A Polymer Chemistry, 2011.
Kozlovskaya et al., Self-assemblies of thermoresponsive poly(N-vinylcaprolactam) polymers for applications in biomedical field, ACS. Appl. Polym. Mater., 2019.
Vihola, Studies on Thermoresponsive poly(N-vinylcaprolactam) based polymers for pharmaceutical applications, Disseration.
Beija et al., Supporting Information for Thermoresponsive poly(N-vinylcaprolactam)-coated gold nanoparticles: sharp reversible response and easy tunability, Supplementary Material for Chemical Communications, 2011.
Hurtgen et al., Synthesis of thermo-responsive poly(N-vinylcaprolactam)-containing block copolymers by cobalt-mediated radical polymerization, Journal of Polymer Science Part A: Polymer Chemistry, 2012, 50, 400-408.
Gois et al., Synthesis of well-defined alkyne terminated poly(N-vinylcaprolactam) with stringent control over the LCST by RAFT, RSC Adv., 2016, 6(21), 16996-17007.
Siirila et al., The emulsion polymerization induced self-assembly of a thermoresponsive polymer poly(N-vinylcaprolactam), Polym. Chem., 2019, 10, 766.
Beija et al., Thermoresponsive poly(N-vinylcaprolactam)-coated gold nanoparticles: sharp reversible response and easy tunability, Chem. Commun., 2011, 47, 2826-2828.
Nagase et al., Thermo-responsive polymer brushes as intelligent biointerfaces: preparation via ATRP and characterization, Macromol. Biosci., 2011, 11, 400-409.
Sala et al., Thermosensitive poly(N-vinylcaprolactam) injectable hydrogels for cartilage tissue engineering, Tissue Engineering Part A, 2017, 23(17-18), 935.
Kudyshkin et al., Radical polymerization of N-vinylcaprolactam in the presence of chain-transfer agents, Chem. Pap., 2004, 58(4), 286-291.

\* cited by examiner

|  | 37°C/ 3 day | 4°C/ 5 min | |
|---|---|---|---|
| TCPS | A  | E  | |
| B82-CL123 (0.2w/v% coating) NVCL:BMA= 6 : 4 / 2mg/ml | B  | F  | I  |
| B82-CL123 (0.4w/v% coating) NVCL:BMA= 6 : 4 / 4mg/ml | C  | G  | J  |
| B82-CL123 (0.8w/v% coating) NVCL:BMA= 6 : 4 / 8mg/ml | D  | H  | K  |

| PNVCL-b-PBMA (0.4 w/v% of B82-CL123) | PNVCL (4mg/ml) | PBMA (4mg/ml) |
|---|---|---|
| 37°C/ 3 day  | 37°C/ 3 day  | 37°C/ 3 day  |
| 4°C/ 5 min  | 4°C/ 5 min  | 4°C/ 5 min  |

FIG. 5

THERMO-SENSITIVE CELL CULTURE SUBSTRATE HAVING BLOCK COPOLYMER

CROSS-REFERENCE TO RELATED APPLICATIONS

This non-provisional application claims priority under 35 U.S.C. § 119(a) on Patent Application No(s). 201911163920.4, filed in China on Nov. 25, 2019, the entire contents of which are hereby incorporated by reference.

BACKGROUND

1. Technical Field

This present disclosure relates to a thermo-sensitive block copolymer, more particular to a cell culture substrate coated with the thermo-sensitive block copolymer.

2. Related Art

Recently, animal cell culture techniques have been remarkably developed, and also research and development related to animal cells have been carried out in a wide variety of fields. The animal cells have been used not only for commercializing them at the early stage of development or for commercializing products from the cells, but also for analyzing cells and their surface proteins to design useful medicines or for performing treatment by growing the cells of patients in vitro or enhancing the function of the cells, followed by returning the cells into the bodies of the patients. At present, many researchers pay attention to the techniques for culturing animal cells.

Many animal cells, including human cells, are anchorage-dependent cells. Therefore, in order to culture animal cells in vitro, the cells need to be once attached to a scaffold substrate. Under such a background, many researchers have previously designed and devised substrate surfaces that are more desirable for cells. Cultured anchorage-dependent cells produce adhesive proteins when they adhere to a substrate. Therefore, in conventional techniques, the adhesive proteins need to be destroyed, e.g., by enzymatic treatment or the like for detaching the cells.

SUMMARY

According to one aspect of the present disclosure, a method of preparing the block copolymer includes the following steps: obtaining a hydrophobic polymer by atom transfer radical polymerization (ATRP) with typical haloalkane as an initiator, and subsequently obtaining a block copolymer by polymerization of a plurality of thermo-sensitive monomers by using the hydrophobic polymer as a macroinitiator.

According to another aspect of the present disclosure, a block copolymer includes at least one hydrophobic polymer segment containing a hydrophobic polymer and at least one thermo-sensitive polymer segment containing a thermo-sensitive polymer. The hydrophobic polymer is poly n-butyl methacrylate (PBMA). The thermo-sensitive polymer is poly-N-vinylcaprolactam (PNVCL).

According to another aspect of the present disclosure, a thermo-sensitive cell culture substrate includes a base material and a block copolymer. The surface of the base material is coated with the block copolymer, and the block copolymer is prepared by the aforementioned method. The thermo-sensitive polymer of the block copolymer is PNVCL.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

According to one embodiment of the present disclosure, a thermo-sensitive cell culture substrate is provided, and the thermo-sensitive substrate includes a base material and a block copolymer.

The base material can be polystyrene, polycarbonate, polymethyl methacrylate, polyethyleneterephthalate, glass, modified glass and the like, which are usually used for cell culture but also materials which can be formed in arbitrary shapes including, but not limited to, polymer compounds other than the above, ceramics metals, and the like, can also be used. The shape of the base material of the cell culture substrate is not limited to cell culture dishes such as petri dishes, but a multi-well plate (well-shaped base material), fiber (filamentous base material), porous particle (granular base material), tube-shaped base material, or film-shaped base material, or even a combination of two or more thereof is also suitable. A base material in the shape of a container commonly used for cell culture (such as flask, bottle, etc.) is also acceptable. In some embodiments, the base material of the cell culture substrate can be one well-shaped base material or a combination of two or more multi-wells shaped base materials.

The block copolymer includes at least one hydrophobic polymer segment containing a hydrophobic polymer and at least one thermo-sensitive polymer segment containing a thermo-sensitive polymer. The block copolymer normally means a polymer of having at least two compositionally different segments. As understood by those experienced, instances of the block copolymer include diblock copolymers, triblock copolymers, random block copolymers, star-branched block copolymers, and hyperbranched block copolymers. A block copolymer used in the present disclosure typically has a hydrophobic polymer segment (A) and a thermo-sensitive polymer segment (B). The block copolymer may also have any one of the following structures: A-B structure containing two-block segment; A-B-A or B-A-B containing three block segments and -(A-B)n (n as an integer of 2 or more) containing a plurality of blocks. In some embodiments, the block copolymer used for cell culture preferably has the above-mentioned A-B structure. As used herein, the block copolymer having A-B structure includes, for example, a Poly-N-butyl methacrylate (PBMA) segment as a hydrophobic polymer segment (A) and a Poly-N-vinyl caprolactam (PNVCL) segment as a thermo-sensitive polymer segment (B), the block copolymer may be denoted as "B82-CL123", using the number of monomer units in each polymer (that is, 82 units of BMA and 123 units of NVCL). The PNVCL is a kind of thermo-sensitive polymer which not only has a phase transition temperature close to physiological temperature but also has good biocompatibility and non-toxicity.

The hydrophobic polymer used herein is not particularly limited as long as it is not dissolvable in water. Some examples of the hydrophobic polymer include polyalkyl acrylates such as poly-n-butyl acrylate and poly-t-butyl acrylate; polyalkyl methacrylates such as poly-n-butyl methacrylate, poly-t-butyl methacrylate, and polymethyl methacrylate; polystyrenes and similar.

The thermo-sensitive polymer used herein means a polymer having a lower critical solution temperature (LCST) and/or a polymer having an upper critical solution temperature (UCST). It may also be any of homopolymers, copolymers, and mixtures. Specifically, such polymers are obtained by, e.g., homopolymerization or copolymerization of monomers as described below. Instances of the monomers to be used include vinyl caprolactam compounds, vinyl pyrrolidone derivatives, vinyl ether derivatives, 3-methyl-n-vinylcaprolactam derivatives. For the copolymers, any two or more of these monomers may be used. As to addition copolymers with monomers other than the above-mentioned monomers, graft-polymers or co-polymers of polymers, or mixtures of polymers and/or copolymers, may also be used. Furthermore, the polymers may be optionally cross-linked as long as the inherent properties of the polymers are not impaired. After all, a substance to be separated is usually a biological substance, it is preferable to select a thermo-sensitive polymer suitable for separating a biological substance of interest in a temperature range of 4° C. to 50° C. In the present disclosure, the thermo-sensitive polymer may also be used with any one or a combination of two or more of poly-N-substituted vinylcaprolactam derivatives, poly-N-substituted vinyl pyrrolidone derivatives, poly-3-methyl-n-vinyl caprolactam derivatives, and their copolymers.

Generally, reversible addition-fragmentation chain transfer (RAFT) polymerization, atom transfer radical polymerization (ATRP), nitroxide mediated radical polymerization (NMP), cobalt salt regulated active radical polymerization and anionic polymerization are used to prepare the block copolymers. When the block copolymers are produced by ATRP, some functional groups based on the initiator of ATRP remain at the end of the block copolymers, which is unique to the ATRP method. After the ATRP, further polymerization can be started from the end. Therefore, according to the present disclosure, a new functionality can be given to the surface of the thermo-sensitive cell culture substrate. Some examples of functional groups include, but are not limited to, hydroxyl, carboxyl, amino, carbonyl, aldehyde, sulfonic, etc. In addition, the peptide or protein which can accelerate cell adhesion can also be fixed on the end of the polymer chain. In this case, the introduction of functional groups in the end of the polymer chain will provide a different way to control the surface of the thermo-sensitive substrate from different perspectives, because the lower critical solution temperature (LCST) of the polymer, such as the poly (N-vinyl caprolactam). This varies according to the hydrophilicity and hydrophobicity of the end functional groups.

According to the present disclosure, a method of preparing the block copolymer is provided. The hydrophobic polymer is obtained by ATRP with chloroalkane as initiator. Then, the block copolymer is obtained by polymerization of a plurality of thermo-sensitive monomers by using the hydrophobic polymer as a macroinitiator Generally, there are five variable components of ATRP. These variable components are monomer, initiator, catalyst, ligand, and solvent.

More specifically, in one embodiment of the present disclosure, the hydrophobic polymer is PBMA, and the thermo-sensitive monomer is NVCL. The polymerization of PBMA with NVCL is also ATRP polymerization. The present disclosure develops suitable polymerization conditions to afford well-controlled PNVCL via ATRP polymerization with the PBMA as a macroinitiator to graft the VCL monomers forming the block polymer. The ATRP method used here presents several characteristics: (a) need of post-polymerization reactions to functionalize the polymer; (b) facilitates the synthesis of complex structures from a simple ligand, copper-catalyzed chloro-alkane reaction; and (c) expands the range of applications of this temperature-responsive polymer.

Generally, a conventional copolymerization of BMA with NVCL cannot achieve high yield rate. When two monomers have different reactivity, their copolymerization is hard to control since the different monomer reactivity will drive the polymerization preferentially toward the monomers with the higher reactivity. Although NVCL is a non-conjugated monomer that has a rapid polymerization rate in radical polymerization reactions, NVCL propagation radicals is unstable, which can inhibit its polymerization when it encounters the monomers that produce more stable propagation radicals, such as BMA. As to the conventional copolymerization, the lower content of PNVCL was observed in its copolymer with PBMA even when the feeding ratio of NVCL was nine fold more than that of BMA with the overall conversion of NVCL monomer of only 2%. In one embodiment of the present disclosure, PBMA, obtained by ATRP with chloroalkane as initiator, enjoys relatively similar reactivity with NVCL, such that high yield rate is observed in the polymerization of PNVCLs by using PBMA as a macroinitiator.

The block copolymer can be obtained by the ATRP, such as the method of living free-radical polymerization in the presence of the ATRP initiator to grow the thermo-sensitive block copolymer. The solvent used for polymerization in the disclosure is not specially defined, but preferably benzene, 1.4-dioxane, dimethylformamide (DMF), etc. Giving to the types of monomers and ATRP initiators used in polymerization, solvents can be appropriately selected. The disclosure is a method for growing polymers with hydration force varying in the temperature range of 0-80° C. from monomers by activating free radical polymerization. This polymerization is initiated in 1.4-dioxane and other solvents in the presence of ATRP initiators, catalysts, ligands, and other reagents. The concentration of initiator, catalyst/ligand, reaction temperature and reaction time in the polymerization process are not limited but can be changed depending on the purpose. Furthermore, the reaction liquid can be kept still or stirred. Relating to the present disclosure, the thermo-sensitive material for cell culture is generally obtained by dissolving or dispersing in a solvent, which a block copolymer is obtained as described above to uniformly coat the substrate surface with the copolymer. The solvent is not particularly limited but can be appropriately selected from a solvent capable of dissolving or dispersing block copolymers without dissolving the substrate surface. Some examples of solvents include N, N-diethylacrylamide, isopropanol, ethanol, acetone, tetrahydrofuran, 1,4-dioxane, dimethyl sulfoxide, methylethyl ketone, N, N-Dimethylacetamide, chloroform, dichloromethane or acetonitrile, N, N-dimethylformamide, etc. When using multiple solvents, there is no particular limit on the mixing ratio of solvents. Although, we prefer to use ethanol because it is more environmental friendly.

The surface of the base material is coated with the block copolymer in an amount of 1.0 to 4.0 μg/cm² of the thermo-sensitive polymer. In detail, the block copolymer is a hydrophobic polymer segment which is paired with an amount of 1.0 to 4.0 μg/cm² of thermo-sensitive polymer segment. The advantage is that the hydrophobic polymer moiety of the block copolymer which coats on the base material is not detached from the surface not only during the cell culture step but also the detachment process of cultured cells or a cell sheet by the change of temperature.

The surface of the base material is coated with the block copolymer in an amount of 1.0 to 4.0 μg/cm² of the thermo-sensitive polymer. In some embodiments, the surface of the base material is coated with the block copolymer in an amount of 2.0 to 3.5 μg/cm² of the thermo-sensitive polymer; in some other embodiments, the surface of the base material is coated with the block copolymer in an amount of 3.0 to 3.5 μg/cm² of the thermo-sensitive polymer. When the amount of thermo-sensitive polymer is less than 1.0 μg/cm², it is challenging for cultured cells on the block copolymer to be detached by the change of temperature. Thus, making the operation efficiency noticeably deteriorated, and such case is unfavorable. In contrast, in the case of more than 9.0 μg/cm², it is difficult for cells to adhere to the polymer region. Since it becomes difficult to adhere to cells to the polymers, such a case is unfavorable for the cell culture substrate of the present disclosure. The coating amount may be measured according to the generally known procedure or any other method may be used. For instance, an FT-IR-ATR method, an elemental analysis method, ESCA. and the similar may be used.

The content of the thermo-sensitive polymer in the block copolymer is from 50 to 80 wt %. In some embodiments, the content of the thermo-sensitive polymer in the block copolymer is from 55 to 70 wt %; in some other embodiments, the content of the thermo-sensitive polymer in the block copolymer is from 60 to 65 wt %. In the case of less than 15 wt %, it will be challenging for cultured cells on the polymer to be detached by the change of temperature. Thus, it will make the operation efficiency noticeably deteriorated, and such case is unfavorable. In contrast, in the case of more than 90 wt %, it is difficult for cells to adhere to the polymer region. Since it becomes difficult to adhere cells to the polymers, it is unfavorable for the cell culture substrate in the present disclosure. Such a case is also unfavorable because the amount of a hydrophobic polymer moiety in the block copolymer is low and the block polymer may be easily detached from the substrate surface.

Then, the block copolymer is obtained According to the present disclosure, the base material of the thermo-sensitive cell culture substrate is coated with the block copolymer. As to the block copolymer, the hydrophobic polymer segment is paired with the thermo-sensitive polymer segment in a predetermined ratio. When the content of the thermo-sensitive polymer in the block copolymer is more than 80 wt % (where the content of the hydrophobic polymer in the block copolymer is less than 20 wt %) the block copolymer is likely to be detached from the base material surface of the substrate as described above. Therefore, 20-50 wt % of the hydrophobic polymer in the block copolymer is suggested. In addition, when the cell sheet is produced according to the present disclosure, the amount of the coated thermo-sensitive polymer, which is a main constituent of the block copolymer, is essential. The content of the hydrophobic polymer in the block copolymer may be appropriately adjusted, so that the base material of the culture substrate can be coated with the thermo-sensitive polymer with the above-mentioned desired amount range. More specifically, the surface of the base material of the thermo-sensitive cell culture substrate can be coated with the above-mentioned block copolymer in an amount of 0.5 to 3.0 μg/cm² of the hydrophobic polymer. In some embodiments, the surface of the base material is coated with the above-mentioned block copolymer in an amount of 0.7 to 2.0 μg/cm² of the hydrophobic polymer; in some other embodiments, the surface of the base material is coated with the above-mentioned block copolymer in an amount of 0.9 to 1.5 μg/cm² of the hydrophobic polymer.

According to one embodiment of the present disclosure, the thermo-sensitive polymer in the block copolymer may have an average molecular weight of 6000 or more. In some other embodiments, the average molecular weight of the thermo-sensitive polymer in the block copolymer is 8000 or more; in some other embodiments, the average molecular weight of the thermo-sensitive polymer in the block copolymer is 10000 or more; in still some other embodiments, the average molecular weight of the thermo-sensitive polymer in the block copolymer is 12000 and more. If the average molecular weight is less than 3000, it is challenging for cultured cells on the polymer to be detached by the change of temperature. Thus, making the operation efficiency noticeably deteriorated, and such case is unfavorable. In addition to the accordance with the present disclosure, when the molecular weight of the thermo-sensitive polymer has the above-mentioned lower limit, cultured cells can be easily detached without limitation by the upper limit of the molecular weight. In one embodiment, the upper limit of the average molecular weight of the thermo-sensitive polymer may be 35000, 30000 or 25000.

As described above, the block copolymer of the present disclosure includes a hydrophobic polymer segment and a thermo-sensitive hydrophilic polymer segment. When the surface of the base material is coated with the block copolymer and dried, it is expected to develop a phase separation structure on the base material, such as a fine lamella structure, a cylinder structure, a sea-island structure, or a co-continuous structure. There are no special restrictions on the morphology and size of the phase separation structure. When the cells adhere to the substrate surface, the existence of the phase separation structure on the substrate surface is more preferable because it can obstruct the decline of cells.

In accordance with the present disclosure, it is necessary to apply the above-mentioned block copolymer solution homogeneously to a base material surface. Some methods for applying the solution include, but are not particularly limited to, the method of utilizing a spin coater, the method of leaving a base material standing on a horizontal table, and other similar methods. The thermo-sensitive cell culture substrate according to the present disclosure is obtained by removing the solvent after the application of the block copolymer solution. Some methods for removing the solvent include but are not limited to, the method of slowly evaporating a solvent at room temperature in the atmosphere, a method of slowly evaporating a solvent at room temperature in a solvent saturated condition, a method of evaporating a solvent by heating, a method of evaporating a solvent by reducing pressure, and other similar methods. The former two methods are preferable for producing a clean surface of the thermo-sensitive cell culture substrate. Although, the method of slowly evaporating a solvent at room temperature in a solvent saturated condition is considered to be more preferable.

When the above-mentioned base material of the thermo-sensitive substrate is coated with block copolymers, the modified surface of the base material becomes hydrophobic. Therefore, as to a base material with a hydrophilic surface, such as a glass plate is used, it is better to be subjected to hydrophobization treatment beforehand. The hydrophobization treatment may be, without particular limitation, a treatment using a silane coupling agent (e.g., hexyltriethoxysilane).

Cells that can be cultured on the surface of the thermo-sensitive substrate obtained by the present disclosure are not limited by their origin. In the present disclosure, a source and a preparing method of the cells are not particularly limited to the cells like animal cells, insect cells, plant cells, bacteria. Normally, animal cells are better to be originated from humans, monkeys, dogs, cats, rabbits, rats, nude mice, mice, guinea pig, pig, sheep, Chinese hamster, bovine, marmoset, African green monkey, and the like. In addition to the present disclosure, a medium used is not particularly limited as long as it is a medium for animal cells. Such medium could be, for instance, a serum-free media, serum containing media, or other similar media. A differentiation-inducing substance such as retinoic acid or ascorbic acid may also be further added to such a medium. The seeding density of cells on the substrate surface can be appropriately changed, and the seeding density can be determined according to a typical procedure.

According to the present disclosure, when the thermo-sensitive cell culture substrate is used, the cultured cells or a cell sheet can be detached without using any enzymatic treatment and solely by changing the temperature of the culture substrate to the upper critical solution temperature or more, or to the lower critical solution temperature or less of the culture substrate that is polymer-coated on the base material. The above-mentioned detachment can be performed in culture fluid or in another isocratic liquid. This can be performed depending on the purpose. For the purpose of detaching and collecting cells more efficiently and quickly, the method of tapping or shaking the substrate, a method of stirring a medium using a pipette, or the like may also be used separately or in combination.

Cells attained from each tissue can be easily cultured by using the thermo-sensitive cell culture substrate according to the present disclosure. The use of this culturing method makes it possible to detach cultured cells or a cell sheet efficiently without making any damage by solely changing the temperature. In the past, such an operation will need to depend on the efforts of a skillful operator. However, the present disclosure would not require them, and it can also handle large amounts of cells. The culture substrate surface of the present disclosure can be produced by a living radical polymerization method. In particular, the culture substrate surface can be effortlessly and precisely designed, and a functional group can be conveniently introduced into a molecular chain terminal by an ATRP method (one of living radical polymerization methods). As a result, according to the present disclosure the thermo-sensitive cell culture substrate and the producing method is extraordinarily advantageous to cell culture techniques.

The following specific embodiments are provided for further explanation of the present disclosure. Also, several issues are discussed to understand the characteristics and technical effects of the thermo-sensitive cell culture substrate.

[Issue 1] Preparation and Characteristics of Thermo-Sensitive Surface

Block copolymers are prepared and spin-coat on the surface of the base material to obtain the thermo-sensitive substrate. The block copolymer includes a segment of PNVCL as the thermo-sensitive polymer segment, and a segment of PBMA as the hydrophobic polymer segment. For the surface coated with the block copolymers, the physical properties, such as amount of the polymers and surface wettability, are introduced on the surface. The temperature-dependent change of cell adhesiveness to the substrate surface is also inspected.

Figure 1:
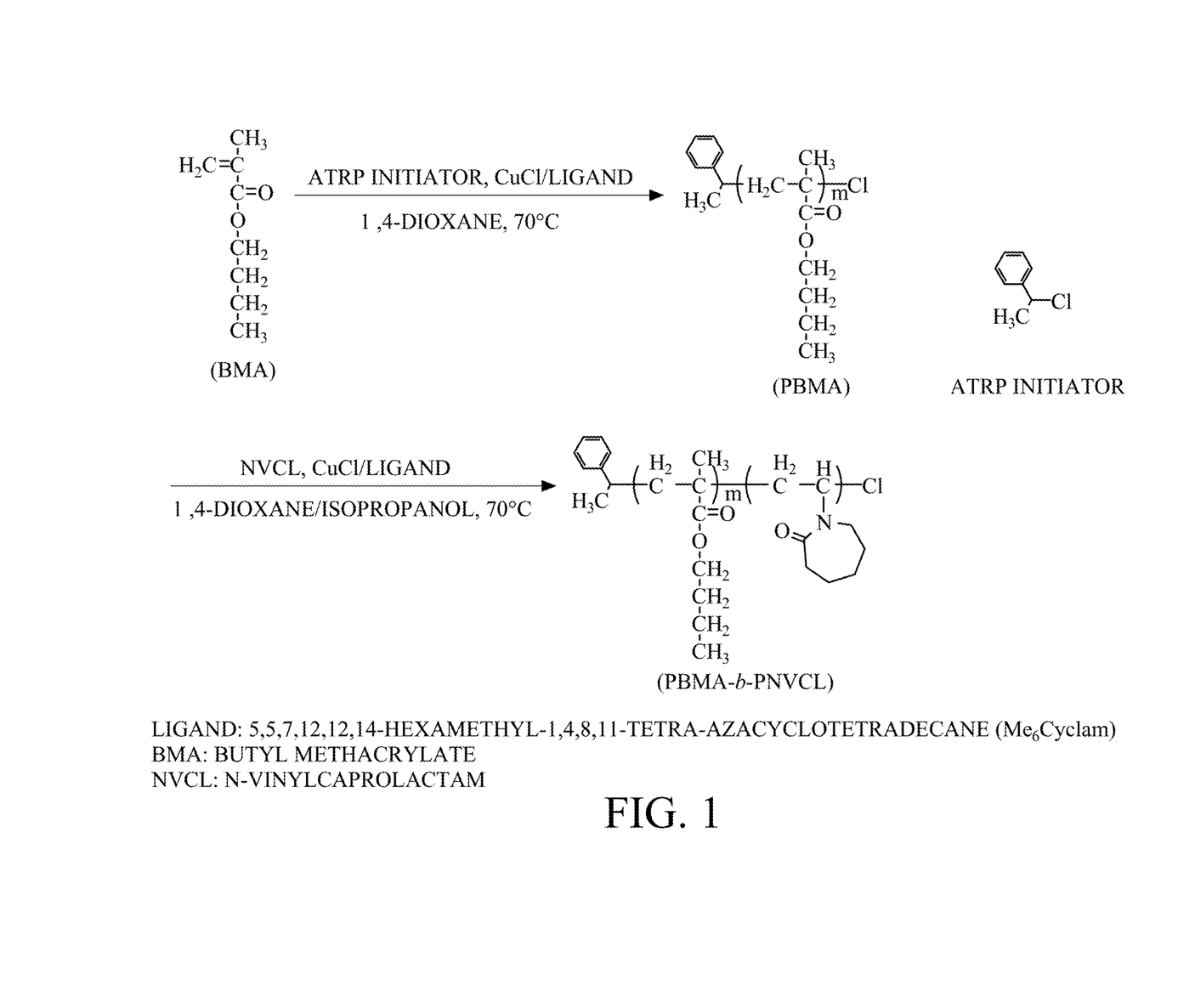
FIG. 1 shows a synthetic route of block copolymers according to the present disclosure.

FIG. 1 shows a synthetic route of block copolymers according to the present disclosure. Referring to the preparation of block copolymers, PBMA-b-PNVCL block copolymers are prepared by using PBMA, synthesized by ATRP, as a macromolecular initiator. Additionally, the molecular weight is controlled by ATRP. In the embodiment of FIG. 1, the initiator of ATRP is 1-chloro-1-phenylethane, and the catalyst of ATRP is cuprous chloride and 5, 5, 7, 12, 12, 14-hexamethyl-1, 4, 8, 11-tetra-azacyclotrtradeane ($Me_6$Cyclam).

Referring to the characteristics of block copolymers, the obtained polymers are evaluated by nuclear magnetic resonance spectrometry (1H-NMR) and gel permeation chromatography (GPC). PBMA-b-PNVCL is dissolved at each concentration of 0.2 w/v %, 0.4 w/v % or 0.8 w/v % in a solvent of ethanol. Additionally, a PBMA solution (0.4 w/v %) and PNVCL solution (0.4 w/v %) are similarly prepared as controls (comparative examples).

The surface of a polystyrene (TCPS), used as a base material for cell culture, is spin-coated with the polymer solution (3000 rpm, 30 sec) and dried overnight at room temperature. The TCPS is later washed with water and dried under reduced pressure at room temperature for 6 hours in order to achieve a thermo-sensitive surface. In addition, TCPS without coated with the polymer solution is used as control (comparative example).

To examine the stability of polymer coatings in water, the substrate is left standing in water at 37° C. for 24 hours. It is then shaken in water at 4° C. for 6 hours and then dried under reduced pressure. At first, the amount of polymers on the surface of the base material is determined by an attenuated total reflection Fourier to transform infrared spectroscopy (ATR/FTIR) method in order to study a difference between polymer amounts before the treatment and those after the treatments.

TABLE 1 below shows the number of monomers in the block copolymer and the average molecular weight of the block copolymer according to the present disclosure.

TABLE 1

| SAMPLE NAME | Number average molecular weight $(Mn)^a$ | Molecular weight distribution $(Mw/Mn)^b$ | NUMBER OF MONOMERS | | RATE OF PNVCL IN POLYMER (wt %) |
|---|---|---|---|---|---|
| | | | BMA | NVCL | |
| B82-CL82 | 23100 | 1.22 | 82 | 82 | 49 |
| B82-CL123 | 28800 | 1.33 | 82 | 123 | 59 |

TABLE 1-continued

| SAMPLE NAME | Number average molecular weight (Mn)[a] | Molecular weight distribution (Mw/Mn)[b] | NUMBER OF MONOMERS BMA | NVCL | RATE OF PNVCL IN POLYMER (wt %) |
|---|---|---|---|---|---|
| B82-CL192 | 38400 | 1.35 | 82 | 192 | 69 |
| B82-CL328 | 57300 | 1.30 | 82 | 328 | 80 |

[a]polymer concentration from spin coating
[b]determined by ATR/FT-IR
Solvent: ethanol spin coating treatment TCPS (3000 rpm, 30 sec)

TABLE 2 below shows the characteristics of the block copolymers according to the present disclosure. The term "B(x)-CL(y)" (both (x), (y) are natural number) represents that PBMA segment in the block copolymer includes a total of (x) BMA monomers, and PNVCL segment in the block copolymer includes a total of (y) NVCL monomers. For example, a PBMA-b-PNVCL block copolymer, with a monomer unit ratio of BMA and NVCL being 82:123, is expressed as "B82-CL123".

TABLE 2

| SAMPLE NAME | CONCEN-TRATION (w/v %)[a] | AMOUNT OF GRAFTED PNVCL [μg/cm²][b] | |
|---|---|---|---|
| | | BEFORE WASH | AFTER WASH[c] |
| B82-CL123 | 0.2 | 2.04 ± 0.10 | 1.93 ± 0.08 |
| | 0.4 | 3.22 ± 0.12 | 3.05 ± 0.13 |
| | 0.8 | 4.5 ± 0.22 | 4.21 ± 0.20 |
| PNVCL | 0.4 | 3.35 ± 0.15 | 0.73 ± 0.03 |

[a]determined by 1H NMR
[b]determined by GPC
[c]soaked in water at 37° C. for 24 hours, immersed in water at 4° C. for 24 hours, and then vacuum-dried. B82-CL123 (MOLECULAR WEIGHT: 28800 g/mol, RATE OF PNVCL IN POLYMER: 59%). PNVCL (MOLECULAR WEIGHT: 13900 g/mol)

The surface wettability at 20° C. and 37° C. is evaluated by using a water contact angle measurement machine. In the investigation to the surface stability of the PBMA-b-PNVCL-coated base materials using ATR/FT-IR, differences in the amount of grafted PNVCL are not observed between the thermos-sensitive substrates before the treatment and those after leaving the substrates standing in water at 37° C. for 24 hours and then shaking them in water at 4° C. for 6 hours. TABLE 3 shows the characteristics of a thermo-sensitive cell culture substrate according to the present disclosure.

TABLE 3

| Sample Name | Polymer Concentration (w/v %)[a] | Amount of grafted PNVCL (μg/cm²)[c] | 20° C. | 37° C. |
|---|---|---|---|---|
| B82-CL82 | 0.4 | 2.52 ± 0.10 | 77.21° | 78.13° |
| B82-CL123 | 0.2 | 1.93 ± 0.08 | 79.16° | 79.54° |
| B82-CL123 | 0.4 | 3.05 ± 0.13 | 78.21° | 77.69° |
| B82-CL123 | 0.8 | 4.21 ± 0.20 | 73.61° | 74.25° |
| B82-CL192 | 0.4 | 3.57 ± 0.15 | 66.21° | 67.43° |
| B82-CL328 | 0.4 | 4.16 ± 0.18 | 67.48° | 68.28° |
| TCPS | — | — | 93.64° | 94.76° |

[a]polymer concentration for spin coating on TCPS (3,000 rpm, 30 sec)
b: determine by contract angle
[c]determine by ATR/FTIR.

As the result points out the block copolymers remained stably coated on the base materials of the thermos-sensitive substrates in water during temperature change across LCST (32° C. in the case of PNVCL) (shown in TABLE 2). This result is likely caused by the stable physical adsorption of PBMA, a hydrophobic polymer chain to the polystyrene used as the base material of thermos-sensitive substrate, through hydrophobic interaction. When the surface wettability is measured for the polymer-coated base materials and it hits at a temperature over and below LCST of PNVCL chain, the difference between them is not observed in the PBMA-b-PNVCL-coated base materials, as with the PBMA coated base materials (shown in TABLE 3). This impressive change is not observed in surface wettability measurement of the PBMA-b-PNVCL-coated base materials which tracks a macro-environmental variation in the PBMA-b-PNVCL coated base materials. This is likely because a PBMA chain and a PNVCL chain are phase-separated in order to develop respective domains on the surface layer of the substrates. Unlike the common thermo-sensitive cell culture substrate that is coated with PNVCL as thermo-sensitive chain. Therefore, it is likely that a phase separation structure can be formed depending on the ratio of PNVCL chain to a block copolymer which consists of PBMA chain and the PNVCL chain (shown in TABLE 1).

[Issue 2] Investigation of Grafted Amount and Cell Behavior

Figure 2:
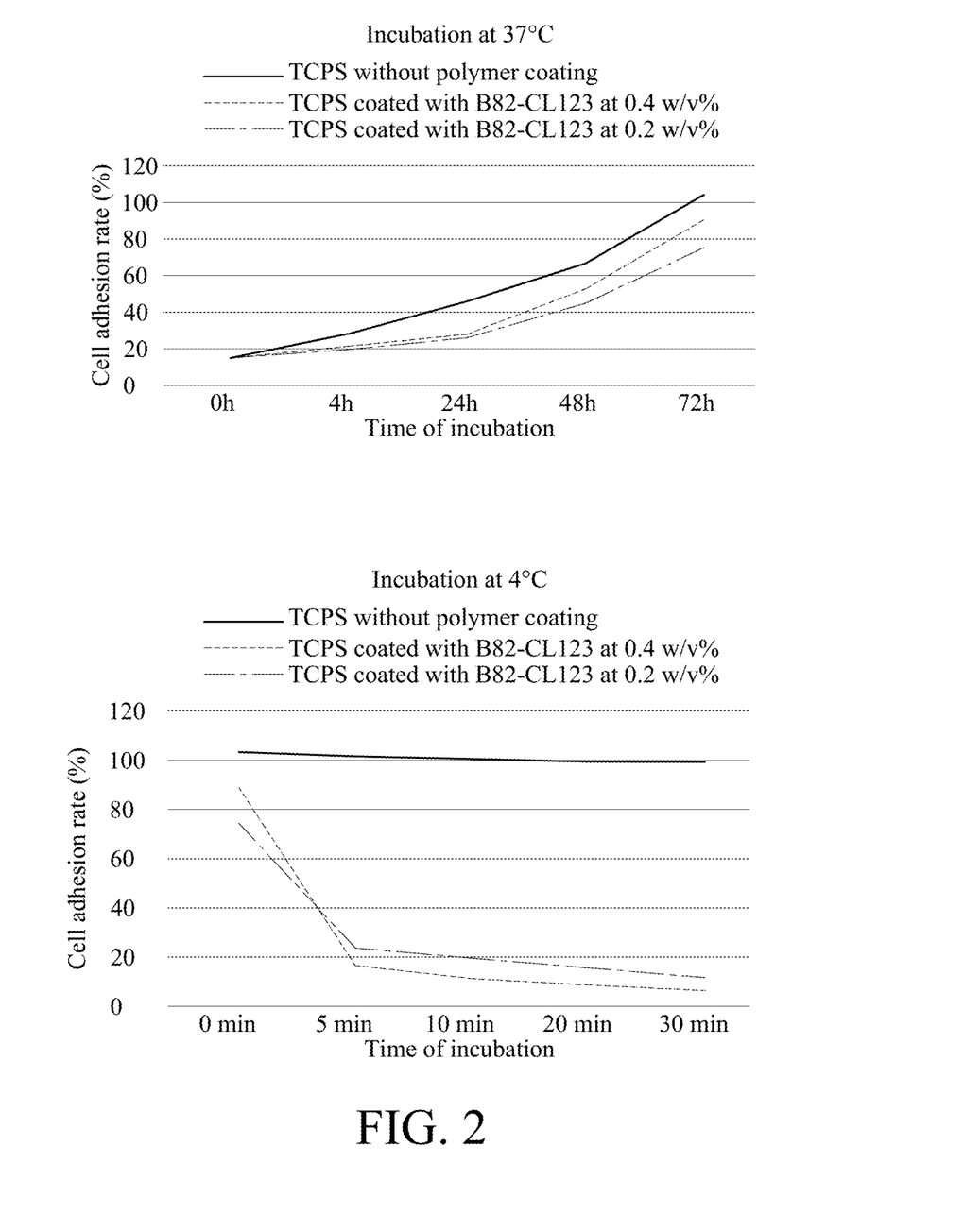
FIG. 2 shows a relationship between cell behavior and the thermo-sensitive substrate according to the present disclosure.

A thermo-sensitive cell culture substrate is provided, and the thermo-sensitive substrate includes TCPS (base material) and B82-CL123 (block copolymer) coating on TCPS. The TCPS is coated with B82-CL123 at various concentrations. Mouse axillary lymph node vessels endothelial cell line (SVEC) are seeded on the thermo-sensitive substrates at a concentration of $1.4 \times 10^4$ cells/cm² and later evaluated the adhesiveness of the cells to polymer-coated substrate surfaces at 37° C. with the desorption behaviors of the cells treated at a low temperature of 4° C. FIG. 2 shows a relationship between cell behavior and the thermo-sensitive substrate according to the present disclosure. The lines in FIG. 2 represent the changes of cell adhesion rate on TCPS without polymer coating and TCPS coated with B82-CL123 at 0.4 w/v % and 0.2 w/v %.

Figure 3:
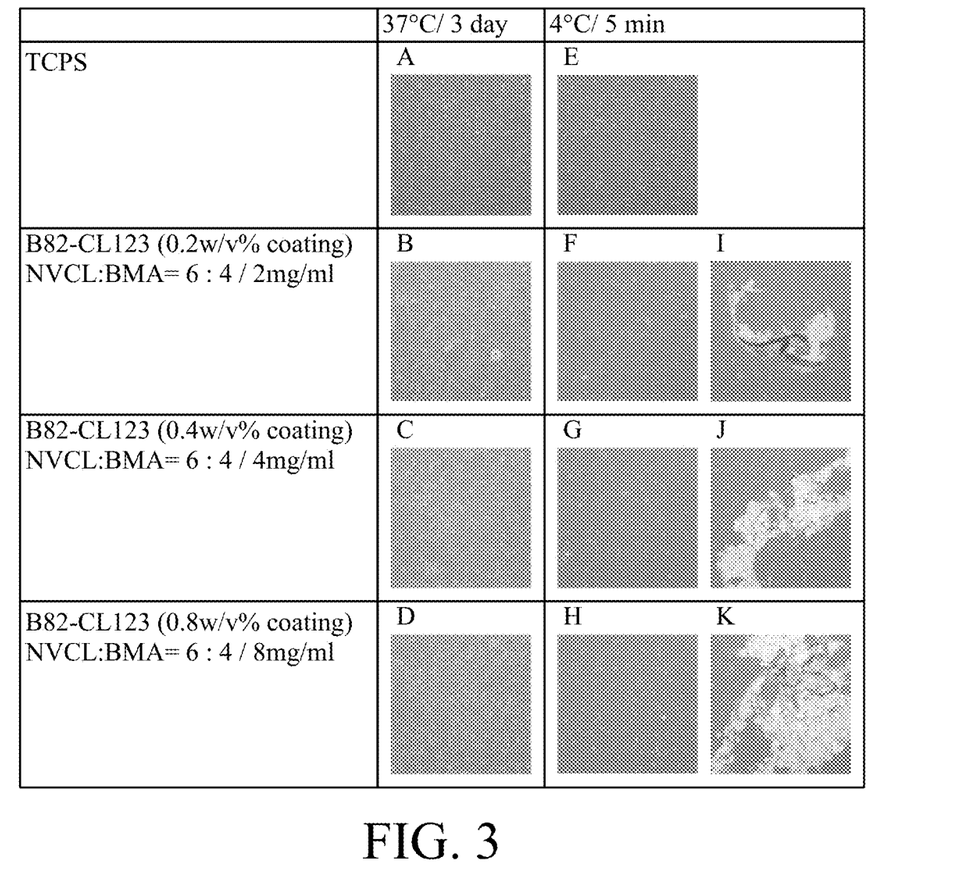
FIG. 3 shows photographs representing a relationship between cell behavior and a thermo-sensitive surface attained in Issue 1.

FIG. 3 shows photographs representing a relationship between cell behavior and a thermo-sensitive surface attained in Issue 1. At each grafted amount of the block copolymer. Represented are the microphotographs of adherent cells at 72 hours after seeding the cells at 37° C. on TCPS (A), and on the thermo-sensitive surfaces which are prepared with the TCPS coated with 0.2 w/v % (B), 0.4 w/v % (C), and 0.8 w/v % (D) of B82-CL123. By decreasing the temperature to 4° C., then culturing for an additional 5 to 10 minutes, the morphologies of the cells after are represented in (E) to (H), respectively. CellSheet detached from the petri dish interface in (I) to (K), respectively. The seeding of the cells measure $1.4 \times 10^5$ cell s/cm².

As shown in FIG. 3, after 72 hours culture, it reveals changes in cell adhesion rate (%) in the case of seeding SVEC cells on each thermo-sensitive substrate and then changing culture temperature from 37° C. to 4° C. More specifically, the cell adhesion rates are increased during the cell culture at 37° C. The adhesion rate is the highest in TCPS for cell culture, and it is relatively higher in TCPS coated with B82-CL123 at 0.4 w/v %. In contrast, the cell adhesion rate is the lowest in TCPS coated with B82-CL123 at 0.8 w/v %.

When the amount of PNVCL coating on TCPS is measured, it is 3.05 μg/cm² at a concentration of 0.4 w/v %, and 4.21 μg/cm² at 0.8 w/v %. These results indicate that the greater amount of coated PNVCL tends to result in a lower cell adhesion rate. Therefore, using the substrate coated with PNVCL whose amount is 3.05 μg/cm², the cell adhesion rate varies when the temperature is changed from 37° C. to 4° C. During the temperature change, the cell adhesion rate is almost not observed in non-coated TCPS. In the case of using the TCPS coated with PNVCL in the amount of 4.21 μg/cm², an immediate detachment of cells is observed when the temperature is changed from 37° C. to 4° C. However, the cell adhesion rate at 37° C. is low, which would not be suitable for culturing cells.

Later on, the desorption of the SVEC cells, which are cultured on the various thermo-sensitive substrates described above, is executed. During the observation of the change in temperature, the results can be visually shown in the photographs. After 3 days culture at 37° C. on the TCPS coated with 0.4 w/v % of B82-CL123, the cell adhesion and spreading are later observed (shown in FIG. 3). Afterward, a thermo-sensitive substrate to which cells adhered is treated with low temperature of 4° C. for 5 minutes. The results found that the cells are desorbed willingly from the substrate surface. When the same operation is carried out in the PBMA coated substrates, cell adhesion and spreading are also observed, while desorption of cells by the low-temperature treatment is not observed (data not shown). Based on the above results, it is likely that the characteristics of the surface has changed to willingly detach the adherent cells as the PNVCL chain brought into the surface is hydrated by the low-temperature treatment of LCST or less.

Figure 4:
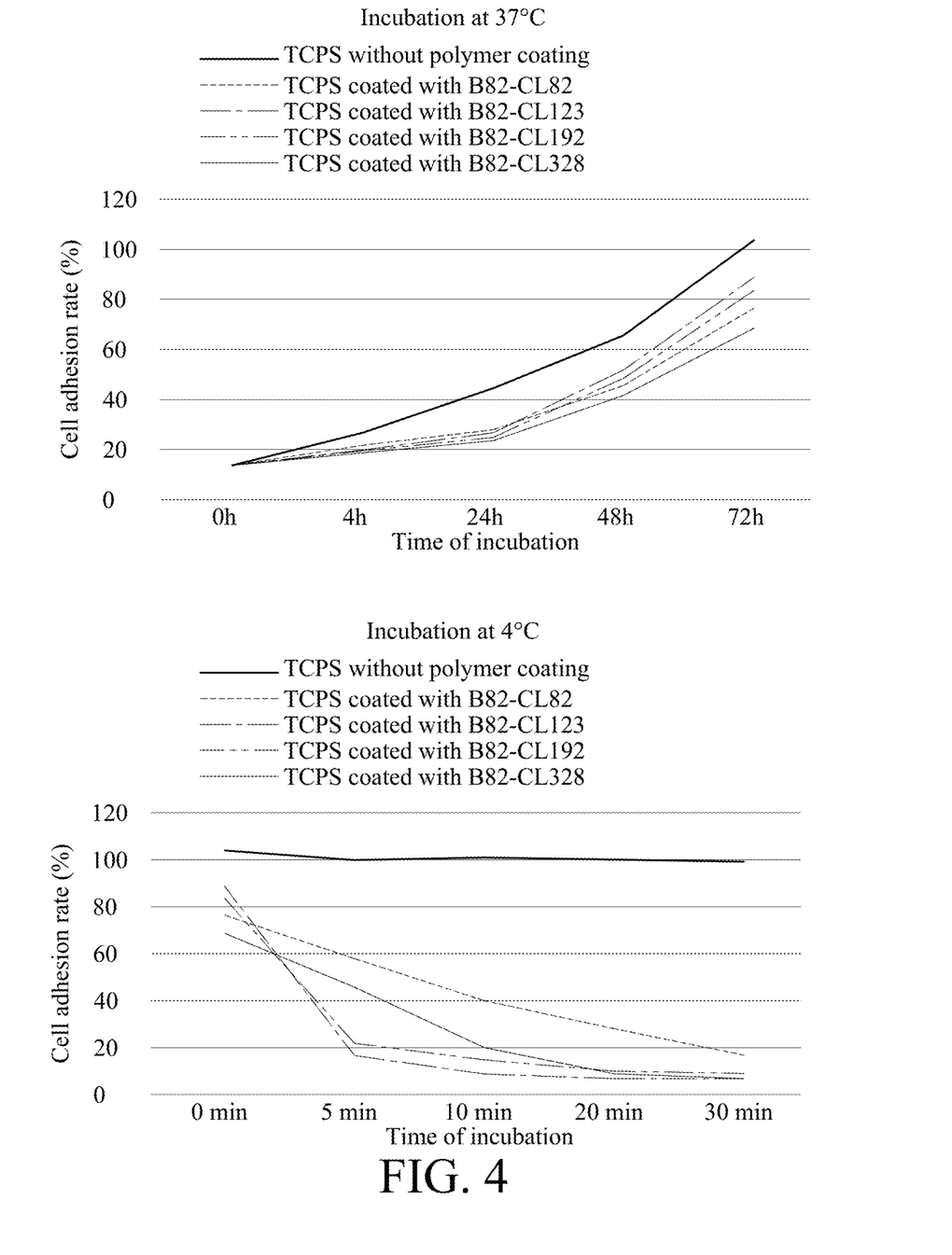
FIG. 4 show the relationships between the molecular chain lengths of thermo-sensitive polymer segment and cell behavior.

[Issue 3] Detailed Analysis of Change of Cell Behavior Depending on Block Copolymers FIG. 4 show the relationships between the molecular chain lengths of thermo-sensitive polymer segment and cell behavior. Relating to the production process, the block copolymers having the constant number of monomer units (the number of monomers) of BMA and the varied number of monomer units of NVCL are prepared. TCPSs are then coated with the block copolymers as described in Issue 1 to examine the change of adhesion rate in the SVEC cells during the change of temperature (shown in FIG. 4). The cell adhesion rate is increased according to the decrease of the coated amount of PNVCL, as with the case of Issue 2. For cell desorption depending on temperature change, it is found that slow desorption occurred in the PNVCL-coated TCPS with the amount is low (2.52 μg/cm²), compared with the PNVCL-coated TCPSs coated with higher amounts (3.05, 3.57, and 4.16 μg/cm²), and this prompt the desorption occurred after the temperature change on the TCPSs coated with high amounts 4.16, 3.57, 3.05 μg/cm², etc.

Figure 5:
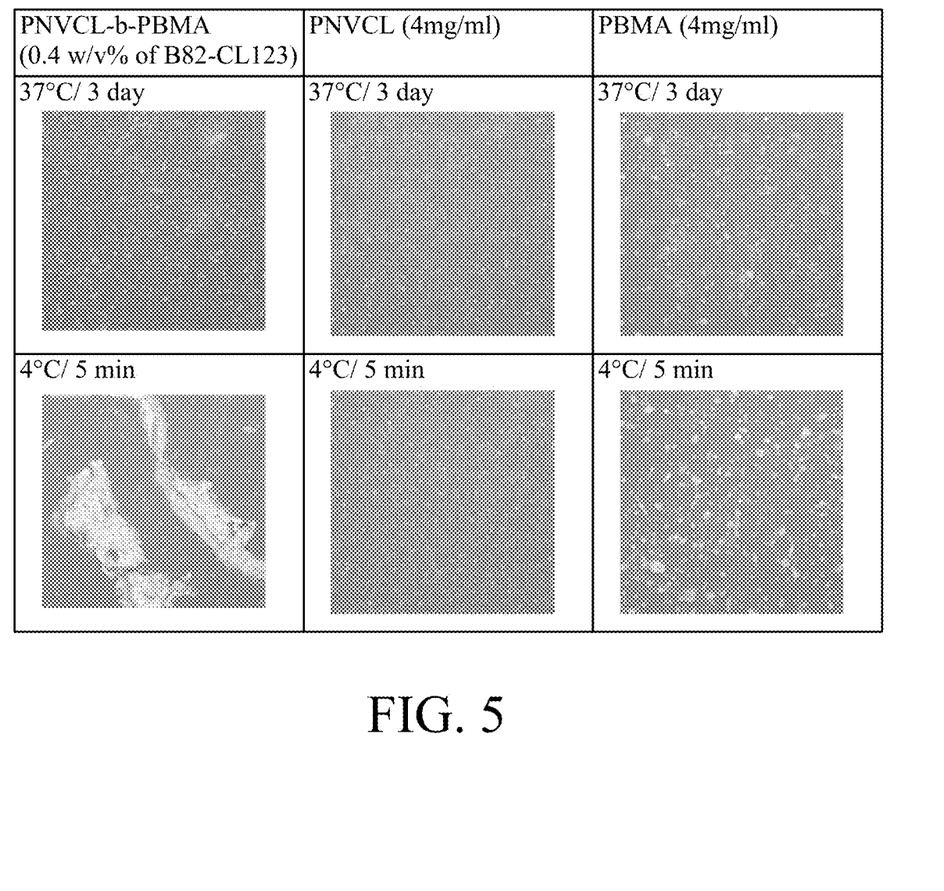
FIG. 5 shows the results of cell culture on the thermo-sensitive substrate according to the present disclosure.

FIG. 5 shows the results of cell culture on the thermo-sensitive substrate according to the present disclosure. Referring to the formation of cell sheets by using block copolymers, a cell sheet formed on the substrate coated with the PBMA-b-PNVCL block copolymer (0.4 w/v % of B82-CL123). The cell sheet is detached by changing the temperature of SVEC cells that are cultured at 37° C. on the TCPS coated with the PBMA-b-PNVCL block copolymer (0.4 w/v % of B82-CL123) until being confluent. Later, it is incubated at 4° C. to form the cell sheet which maintains intercellular junctions between adjacent cells. Various block copolymers with different chain lengths monomer units and grafted amount are prepared.

TABLE 4 below shows the relationships between the thermo-sensitive substrate in the present disclosure through the 3rd embodiment and the formation of cell sheets. TABLE 4 shows the time required for cells to become confluent on the TCPS coated with block copolymer (the period for confluent), and the time from the changing of the temperature at 4° C. to the point of detaching a cell sheet (cell sheet harvest at 4° C.). As a result, it is found that when the amount of coated PNVCL is high (e.g., 4.21 μg/cm² or more), the period until the cells become confluent is 4 days or more. In contrast, when the amount of coated PNVCL is less than 1.0 μg/cm², the cells could not be detached and cell sheet is not developed. In conclusion, the cell culture and the detachment of cultured cells or a cell sheet by solely changing the temperature can be efficiently executed by using a TCPS coated with PBMA-b-PNVCL.

TABLE 4

| Sample Name | Concentraion (w/v %) | Rate of PNVCL in block copolymer (wt %) | Amount of grafted PNVCL (μg/cm²) | Collection of Cell sheet at 4° C. | Time until reaching Confluence (SVEC seeding at 1.4 × 10⁴ cells/cm²) |
|---|---|---|---|---|---|
| B82-CL123 | 0.2 | 59.52 | 1.93 ± 0.08 | yes | more than 3 days |
|  | 0.4 | 59.52 | 3.05 ± 0.13 | yes | 3 days |
|  | 0.8 | 59.52 | 4.21 ± 0.20 | yes | 4 days |
| B82-CL192 | 0.4 | 69.65 | 3.57 ± 0.15 | yes | more than 3 days |
| B82-CL328 | 0.4 | 79.55 | 4.16 ± 0.18 | yes | 4 days |
| B82-CL82 | 0.4 | 49.47 | 2.52 ± 0.10 | Not completely | 4 days |

[Issue 4] Comparative Example: Preparation of Thermo-sensitive Surfaces in Aqueous Solvent The B82-CL123 mentioned in Issue 2 is attempted to be dispersed in water at a concentration of 0.2 w/v %. As a result, the polymer is not dispersed or emulsified in water, and any homogeneous solution is not obtained. A TCPS surface is coated to the obtained solution, but the TCPS surface became heterogeneous to an extent that it is visually observed. Therefore, it is not suitable for the present disclosure.

According to the present disclosure, the thermo-sensitive cell culture substrate includes the base material with its surface coated with block copolymer, and the block copolymer includes thermo-sensitive polymer segment. The cultured cells or a cell sheet can be easily detached by solely changing the temperature of the thermo-sensitive substrate. Therefore, cells attained from each tissue can be easily cultured by using the thermo-sensitive cell culture substrate. This culturing method makes it possible to detach cultured cells or a cell sheet by solely changing the temperature and without doing damage.

It will be apparent to those skilled in the art that various modifications and variations can be made to the present disclosure. It is intended that the specification and examples be considered as exemplary embodiments only, with a scope of the disclosure being indicated by the following claims and their equivalents.

What is claimed is:

1. A thermo-sensitive cell culture substrate, comprising a base material and a block copolymer, wherein a surface of the base material is coated with the block copolymer, a thermo-sensitive polymer of the block copolymer is PNVCL, and the block copolymer is prepared by a method comprising:
obtaining a hydrophobic polymer by atom transfer radical polymerization (ATRP) with chloroalkane as an initiator, and subsequently obtaining the block copolymer by polymerization of a plurality of thermo-sensitive monomers by using the hydrophobic polymer as a macroinitiator.

2. The thermo-sensitive cell culture substrate according to claim 1, wherein the surface of the base material is coated with the block copolymer in an amount of 1.0 to 4.0 µg/cm$^2$ of a hydrophilic polymer and 0.5 to 3.0 µg/cm$^2$ of the hydrophobic polymer.

3. The thermo-sensitive cell culture substrate according to claim 1, wherein a content of the thermo-sensitive polymer in the block copolymer is 50 to 80 wt %.

4. The thermo-sensitive cell culture substrate according to claim 1, wherein a content of the hydrophobic polymer in the block copolymer is 20 to 50 wt %.

5. The thermo-sensitive cell culture substrate according to claim 1, wherein the block copolymer coating on the surface of the base material is dried to form a phase separation structure.

6. The thermo-sensitive cell culture substrate according to claim 1, wherein the thermo-sensitive polymer is selected from the group consisting of poly-N-substituted vinylcaprolactam derivatives, poly-N-substituted vinylpyrrolidone derivatives, poly-3-methyl-N-vinylcaprolactam derivatives, their copolymers, polyvinyl methyl ethers and combination thereof.

* * * * *